United States Patent
Bender, II et al.

(10) Patent No.: US 11,554,231 B2
(45) Date of Patent: Jan. 17, 2023

(54) METHODS AND SYSTEMS FOR ANESTHETIC AGENT LEAKAGE DIAGNOSTICS

(71) Applicant: General Electric Company, Schenectady, NY (US)

(72) Inventors: Thomas Lane Bender, II, Cottage Grove, WI (US); Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 791 days.

(21) Appl. No.: 16/274,161

(22) Filed: Feb. 12, 2019

(65) Prior Publication Data
US 2020/0254201 A1 Aug. 13, 2020

(51) Int. Cl.
*A61M 16/00* (2006.01)
*A61M 16/18* (2006.01)

(52) U.S. Cl.
CPC .... *A61M 16/0087* (2013.01); *A61M 16/0051* (2013.01); *A61M 16/18* (2013.01); *A61M 2202/048* (2013.01); *A61M 2205/15* (2013.01)

(58) Field of Classification Search
CPC ...... A61M 2205/3306; A61M 2205/18; A61M 2205/583; A61M 2205/581; A61M 2205/3317; A61M 2205/3368; A61M 2205/3382; A61M 2205/3386; A61M 2205/3592; A61M 2205/3561; A61M 2205/3553; A61M 2205/502; A61M 2205/3334; A61M 2205/702; A61M 2205/3389; A61M 16/203; A61M 16/0891; A61M 16/208; A61M 16/209; A61M 16/202; A61M 16/22; A61M 16/024; A61M 2016/1025; A61M 2016/103; A61M 2016/1035; A61M 2016/0042; A61M 2016/0039
See application file for complete search history.

(56) References Cited

U.S. PATENT DOCUMENTS

| | | | |
|---|---|---|---|
| 4,825,860 A * | 5/1989 | Falb | A61J 1/00 128/203.12 |
| 5,592,934 A | 1/1997 | Thwaites | |
| 6,422,073 B1 * | 7/2002 | Krahbichler | G01N 21/4133 128/203.15 |
| 6,536,432 B2 * | 3/2003 | Truschel | A61M 16/0051 128/202.22 |
| 6,804,991 B2 * | 10/2004 | Balschat | A61M 1/1601 73/40.5 R |

(Continued)

FOREIGN PATENT DOCUMENTS

WO  WO-2004096322 A1 * 11/2004 ............. A61M 1/14
WO  2009033462 A1  3/2009

*Primary Examiner* — Justine R Yu
*Assistant Examiner* — Matthew D Ziegler
(74) *Attorney, Agent, or Firm* — McCoy Russell LLP

(57) ABSTRACT

Methods and systems are provided for anesthetic agent leakage diagnostics. In one embodiment, a method for diagnosing leaks in an anesthetic vaporizer includes calculating a leakage rate based on measurements of an anesthetic agent level in a sump of the anesthetic vaporizer, the measurements received from a fluid level sensor at a first time and a second time, and outputting a maintenance alert responsive to the leakage rate exceeding a threshold.

18 Claims, 6 Drawing Sheets

(56) References Cited

U.S. PATENT DOCUMENTS

| | | | |
|---|---|---|---|
| 7,546,856 B2* | 6/2009 | Chotenovsky | A61M 16/183 |
| | | | 141/291 |
| 8,033,280 B2* | 10/2011 | Heinonen | A61M 16/0051 |
| | | | 128/204.22 |
| 8,752,544 B2 | 6/2014 | Bottom | |
| 8,867,031 B2 | 10/2014 | Jones et al. | |
| 9,829,370 B2* | 11/2017 | Dudar | G01F 23/32 |
| 2008/0295837 A1* | 12/2008 | McCormick | A61M 16/12 |
| | | | 128/204.21 |
| 2010/0078018 A1 | 4/2010 | Heinonen et al. | |
| 2011/0102796 A1* | 5/2011 | Shang | A61M 16/183 |
| | | | 356/436 |
| 2012/0275927 A1* | 11/2012 | Rhim | F04B 49/10 |
| | | | 417/36 |
| 2013/0255676 A1* | 10/2013 | Kuehl | G01F 23/02 |
| | | | 128/203.12 |

* cited by examiner

METHODS AND SYSTEMS FOR ANESTHETIC AGENT LEAKAGE DIAGNOSTICS

FIELD

Embodiments of the subject matter disclosed herein relate to anesthesia systems, and more particularly, to methods and systems for monitoring leakage of an anesthetic agent from an anesthetic vaporizer.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form at a vaporizing chamber. A carrier gas (e.g., a mixture of oxygen and fresh air) may flow into the vaporizer and blend (e.g., mix and converge) with the anesthetic agent vapors generated by the vaporizer before flowing to the patient, where they may be introduced via inhalation, for example.

Conventional anesthetic vaporizers include a sump for storing the liquid anesthetic agent before it is metered to the vaporizing chamber (e.g., via a pump). An operator (e.g., an anesthesiologist or other clinician) may monitor a level of liquid anesthetic agent in the sump, both before use and during use, to ensure sufficient anesthetic agent is available for delivery to the patient during the medical procedure. For example, the level of the anesthetic agent may be viewed through a glass tube or transparent portion of the sump, referred to as a sight glass.

BRIEF DESCRIPTION

In one embodiment, a method for diagnosing anesthetic agent leakage from an anesthetic vaporizer includes calculating a leakage rate based on measurements of an anesthetic agent level in a sump of the anesthetic vaporizer, the measurements received from a fluid level sensor at a first time and a second time, and outputting a maintenance alert responsive to the leakage rate exceeding a threshold. In this way, anesthetic agent leakage from the anesthetic vaporizer may be accurately detected and tracked for a robust diagnostic.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
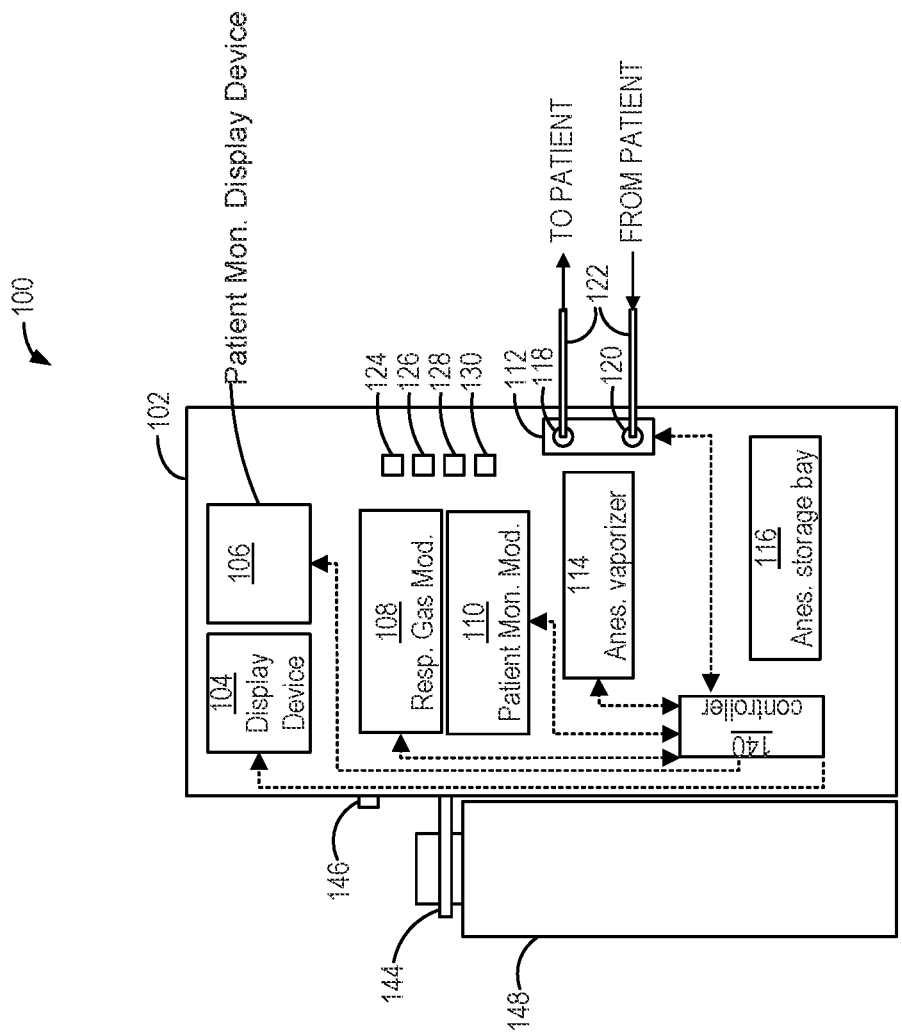
FIG. 1 schematically shows an exemplary embodiment of an anesthesia machine.

The following description relates to various embodiments for detecting and monitoring anesthetic agent leakage from an anesthetic vaporizer, which may be included in an anesthesia machine. Currently available anesthetic agent level indicators, such as sight glasses, do not provide clinicians with sufficient information to determine if anesthetic leakage is occurring. For example, a relatively small change in anesthetic agent level, as viewed through the sight glass, may be unnoticeable. Further, current leak detection methods are manual and not automatic. As one example, a technician may perform a low pressure leak test, during which the technician connects the anesthetic vaporizer to a test device including a squeeze bulb. The technician squeezes the air from the test device and watches for bulb re-inflation to determine if leaks are present. The low pressure leak test cannot be performed while the anesthetic vaporizer is in use (e.g., delivering anesthetic agent to a patient) and does not provide any information about where the leaks may be occurring.

Thus, according to embodiments disclosed herein, an automatic anesthetic agent leakage diagnostic is provided that uses measurements obtained within the anesthetic vaporizer system. In the embodiments disclosed herein, the anesthetic vaporizer includes a sump for storing a liquid anesthetic agent, an electronic fluid level sensor positioned to measure a level of the liquid anesthetic agent stored in the sump, and an electronic controller. According to embodiments disclosed herein, the controller may automatically (e.g., without input from an operator of the anesthetic vaporizer) perform a diagnostic routine to detect anesthetic agent leakage based on measurements received from the fluid level sensor. In some embodiments, the diagnostic routine may include calculating a static leakage rate, referring to a rate of anesthetic agent leakage while the anesthetic vaporizer is shut down and not in use. In other embodiments, the diagnostic routine may include calculating an operational leakage rate, referring to a rate of anesthetic agent leakage while the anesthetic vaporizer is on and in use. The diagnostic routine may further include determining whether anesthetic vaporizer maintenance is indicated based on the calculated leakage rate. Further, in response to anesthetic vaporizer maintenance being indicated, the controller may infer potential leakage sites. Further still, even if anesthetic vaporizer maintenance is not indicated, embodiments disclosed herein include tracking the leakage rate over time to anticipate future maintenance needs.

The embodiments disclosed herein may provide several advantages. For example, the embodiments disclosed herein enable leaks in the anesthetic vaporizer to be detected without any additional effort from an operator or technician. As another example, the embodiments disclosed herein anesthetic agent leakage to be detected while the anesthetic vaporizer is in use. Further, inferring the potential leakage sites may guide the technician during maintenance, which may help expedite repairs. Additionally, by indicating leakage as it occurs and tracking the leakage rate over time to anticipate maintenance needs, anesthetic vaporizer components that are commonly replaced after a set period of time (such as replacing a fill cap every two years) may instead be replaced when they are actually degraded, thereby reducing maintenance costs.

Figure 2:
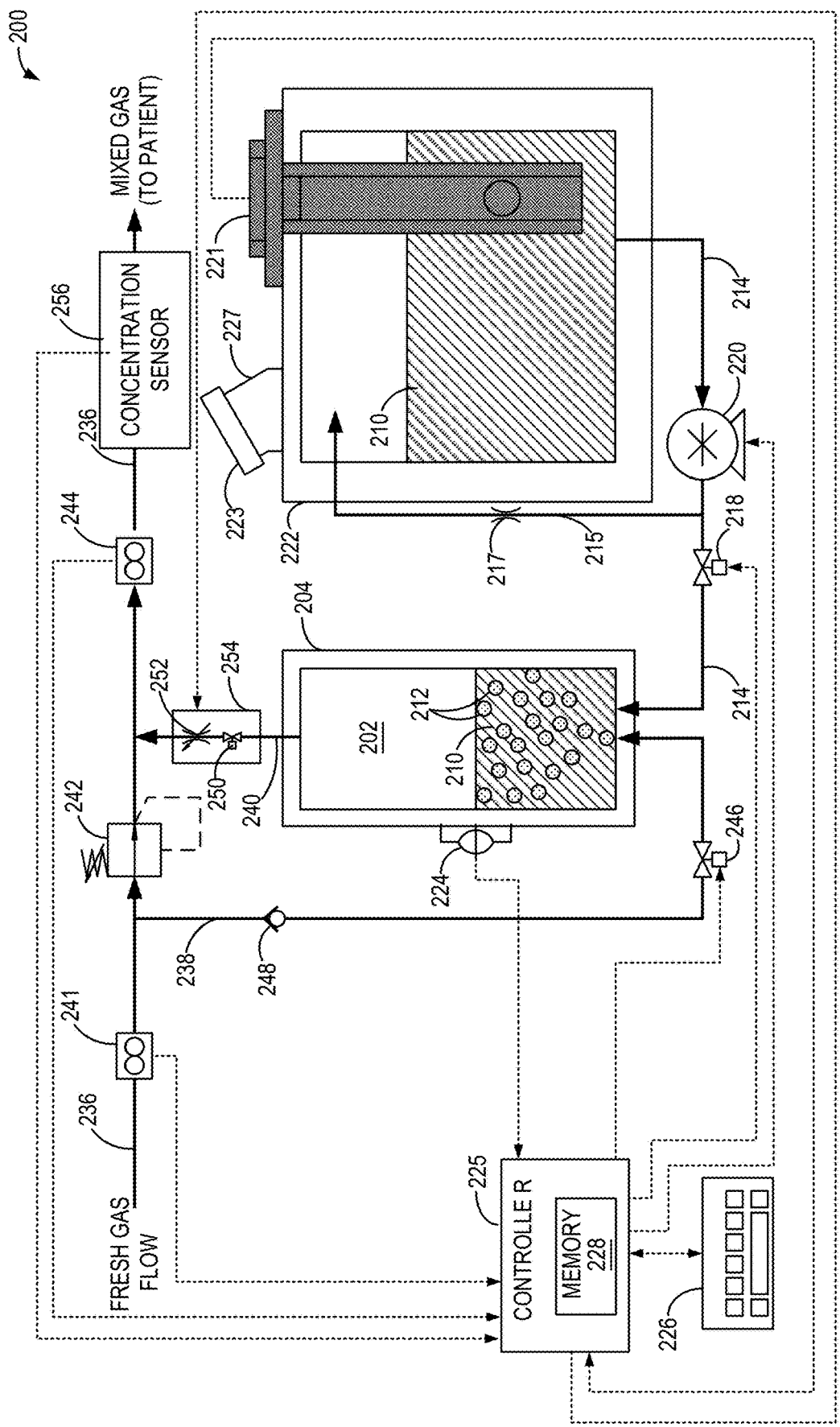
FIG. 2 schematically shows an exemplary embodiment of an anesthetic vaporizer that may be included in an anesthesia machine.
Figure 3:
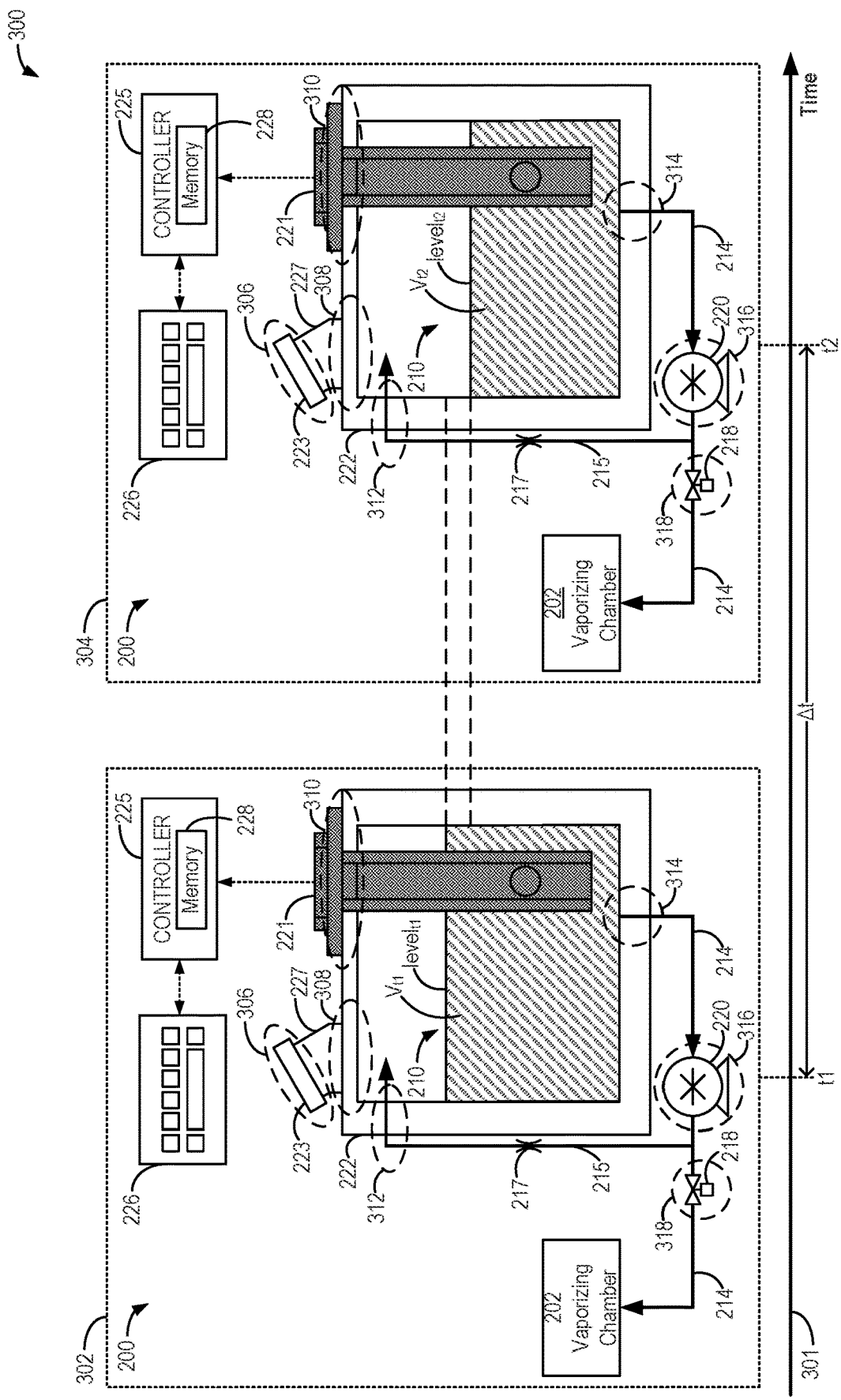
FIG. 3 schematically shows an example timeline for anesthetic agent leakage occurring through one or more potential leakage sites of an anesthetic vaporizer.

FIG. 1 schematically shows an exemplary embodiment of an anesthesia machine. FIG. 2 shows an exemplary embodiment of an anesthetic vaporizer, which may be included in the anesthesia machine of FIG. 1. FIG. 3 schematically shows a decrease in anesthetic agent volume due to leakage at one or more potential leakage sites of the anesthetic vaporizer of FIG. 2. The leakage may be diagnosed according to the example method of FIG. 4. Further, diagnosing the leakage may include calculating a leakage rate based on anesthetic agent level measurements received from a fluid level sensor, such as according to the example method of FIG. 5, and tracking the leakage rate over time, such as according to the example method of FIG. 6.

FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. An example embodiment of anesthetic vaporizer 114 will be described below with respect to FIG. 2. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, a cylinder wrench storage area, and an anesthesia gas scavenging system.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patent (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, the anesthesia monitoring display device 104, and the patient monitoring display device 106.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Anesthetic vaporizers, such as anesthetic vaporizer 114 shown in FIG. 1, may employ various methods to vaporize a liquid anesthetic agent. For example, the anesthetic vaporizer may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). Regardless of the vaporization method, the anesthetic vaporizer 114 may include a sump for storing the liquid anesthetic agent before it is delivered to a vaporizing chamber. Further, in each example, the liquid anesthetic agent may leak from the sump to other components of the vaporizer or to atmosphere, such as when various seals become worn or otherwise degraded.

FIG. 2 shows an exemplary embodiment of an anesthetic vaporizer 200, which may be included in an anesthesia machine (e.g., anesthesia machine 100 shown in FIG. 1). As one example, anesthetic vaporizer 200 may be anesthetic vaporizer 114 of FIG. 1. In the embodiment shown in FIG. 2, anesthetic vaporizer 200 is a bubble-through anesthetic vaporizer, including a vaporizing chamber 202 defined by a housing 204. However, in other embodiments, anesthetic vaporizer 200 may be a gas/vapor blender, a flow-over type anesthetic vaporizer, or any other type of anesthetic vaporizer for use with a volatile liquid anesthetic agent that includes a controller and level sensing technology.

A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example, that is stored in sump 222. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory 228. Controller 225 may be included in (e.g., a part of) or communicatively coupled to controller 140 shown in FIG. 1, for example.

Sump 222 may be refilled via a fill cap 223 and a fill port (e.g., neck) 227. Together, fill cap 223 and fill port 227 may be included in a fill assembly. For example, an operator of anesthetic vaporizer 200 may remove fill cap 223 to refill sump 222 with additional liquid anesthetic agent 210 (e.g., from a refill bottle) via fill port 227 and then replace fill cap 223 to seal sump 222. Fill cap 223 may be a screw cap, for example. Furthermore, pump 220 may decouple vaporizing chamber 202 from sump 222, enabling sump 222 to be refilled while anesthetic vaporizer 200 is in use. Thus, sump 222 may be a sealed system when fill cap 223 is in place and when pump 220 is off (e.g., deactivated) or on (e.g., activated and operating) and between pump pulses.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between and pump 220 and vaporizing chamber 202 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215. Further, liquid return line 215 may include a restriction 217, such as an orifice, to control flow through liquid return line 215 such that liquid anesthetic agent 210 preferentially flows through shut-off valve 218 instead of restriction 217 when shut-off valve 218 is open.

Controller 225 may selectively activate pump 220 to provide liquid anesthetic agent 210 from sump 222 to vaporizing chamber 202 responsive to a measurement received from a level sensor 224. For example, level sensor 224 may be any type of liquid level sensor, such as an optical, ultrasonic, capacitive, float, or pressure-based liquid level sensor positioned to measure a level of liquid anesthetic agent 210 in vaporizing chamber 202. As one example, controller 225 may be configured to maintain the level of liquid anesthetic agent within a threshold range. The threshold range may be defined by a first, lower threshold level and a second, higher threshold level. The first threshold level may be a predetermined, non-zero level of the liquid anesthetic agent that is calibrated to maintain a minimum distance between a bottom of vaporizing chamber 202 and a surface of the liquid anesthetic agent 210 for desired vaporization properties. The second threshold level may be a predetermined, non-zero level of the liquid anesthetic agent that is calibrated to prevent overfilling of vaporizing chamber 202 with liquid anesthetic agent 210 and minimize variation in the desired vaporization properties throughout the threshold range. For example, controller 225 may activate pump 220 in response to the level of anesthetic agent 210 reaching the first, lower threshold level and deactivate pump 220 responsive to the level of anesthetic agent 210 reaching the second, higher threshold level. As another example, additionally or alternatively, controller 225 may activate pump 220 at a duty cycle selected based on the measured level of the liquid anesthetic agent in vaporizing chamber 202 and/or a rate of change of the measured liquid anesthetic agent level to maintain a consistent level of the liquid anesthetic agent 210 in vaporizing chamber 202. For example, the controller may input the measured level of the liquid anesthetic agent, as measured by the level sensor 224, and/or the rate of change into one or more look-up tables, algorithms, or functions, which may output the selected duty cycle. Controller 225 may then activate pump 220 at the selected duty cycle, which may be adjusted as the measured level of the liquid anesthetic agent and/or the rate of change of the measured level changes. For example, as the measured level increases, the duty cycle of pump 220 activation may decrease, and as the measured level decreases, the duty cycle of pump 220 activation may increase. In addition, a positive displacement stepper motor pump may also be used, where each positive displacement step of the pump is equivalent to a specified volume of anesthetic liquid. In this manner, the pump can be used to precisely fill the vaporization chamber and prevent overfill by recording the number of pump steps delivered. This approach may also be used to record a volume of anesthetic agent delivered to the vaporization chamber, which may be valuable for vaporizer run-time/maintenance analysis (service metrics), liquid leak detection, precise determination of an amount of liquid anesthetic remaining and available for delivery, vaporization efficiency calculations, etc.

Anesthetic vaporizer 200 includes a level sensor 221 positioned to measure a level of liquid anesthetic agent 210 in sump 222. Level sensor 221 may be any type of liquid level sensor, such as an optical, ultrasonic, capacitive, float, or pressure-based liquid level sensor, for example. In the embodiment shown in FIG. 2, level sensor 221 is an infrared level sensor. As will be further described below with respect to FIGS. 3-6, output from level sensor 221 may be used for anesthetic agent leakage diagnostics. For example, a decrease in the level of liquid anesthetic agent 210 in sump 222 when anesthetic vaporizer 200 is off (e.g., when pump 220 is deactivated and no fresh gas flow is supplied) may indicate a leak at one or more potential leakage sites described below with respect to FIG. 3. As another example, a decrease in the level of liquid anesthetic agent in sump 222 between pump pulses (or steps) when anesthetic vaporizer 200 is on (e.g., when pump 220 is activated and fresh gas flow is supplied) may indicate a leak at the one or more potential leakage sites.

The more detailed the output of level sensor 221 is, the more accurate or sensitive the anesthetic agent leakage diagnostics will be. For example, a relatively small change in liquid anesthetic agent volume results in a larger change in liquid level height when sump 222 is narrower than when sump 222 is wider. Therefore, the dimensions of sump 222 may be optimized to match the sensitivity of level sensor 221 to detecting level changes in order to be able to detect a desired change in volume. The desired change in volume may be pre-calibrated to represent a small (or slow leak). For example, a 12 mL/week or 0.0012 mL/min change may represent a device performance requirement, and so the sump may be shaped such that level sensor 221 is able to detect at least the 0.0012 mL/min change. As such, for a same volume capacity, sump 222 may be taller and narrower when level sensor 221 is less sensitive to level (e.g., height) changes than when level sensor 221 is more sensitive to level changes.

An upper portion of vaporizing chamber 202 (e.g., above a surface of liquid anesthetic agent 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 146 shown in FIG. 1) and/or one or more gas-holding cylinders (e.g., gas-holding cylinder 148 of FIG. 1). As shown in FIG. 2, the fresh gas flow may enter anesthetic vaporizer 200 via a first gas passage 236. A first mass flow sensor 241 may be coupled to first gas passage 236 to measure a flow rate of the fresh gas flow entering anesthetic vaporizer 200. For example, first mass flow sensor 241 may be an ultrasonic flow meter or a calorimetric (thermal) mass flow meter. A pressure regulator 242 coupled to first gas passage 236 may limit a pressure of the fresh gas downstream of pressure regulator 242. For example, pressure regulator 242 may be a pressure reducing valve such that a pressure of the fresh gas flow downstream of pressure regulator 242 does not exceed a pressure setpoint of the pressure regulator.

A second gas passage 238 branches off from first gas passage 236 between first mass flow sensor 241 and pressure regulator 242 to provide carrier gas to vaporizing chamber 202. As used herein, "carrier gas" refers to a portion of the fresh gas flow that flows to vaporizing chamber 202, whereas "bypass gas" refers to a remaining portion of the fresh gas flow that does not flow through vaporizing chamber 202, as will be elaborated below. For example, second gas passage 238 may pass through an opening in housing 204, which may include a gas-tight seal, to flow the carrier gas through a bottom of vaporizing chamber 202. However, in other embodiments, anesthetic vaporizer 200 may not include second gas passage 238, and carrier gas may not be delivered to vaporizing chamber 202. For example, carrier gas may not be delivered to vaporizing chamber 202 when the liquid anesthetic agent 210 has a relatively low boiling point (e.g., at or around room temperature), such as when liquid anesthetic agent 210 is desflurane or another liquid anesthetic agent of similar volatility.

Second gas passage 238 may include one or more valves disposed therein. As shown in FIG. 2, second gas passage 238 includes a check valve 248 and a shut-off valve 246. Check valve 248 may be a one-way valve that allows the carrier gas to flow from the fresh gas flow to vaporizing chamber 202 and prevents the carrier gas from flowing from vaporizing chamber 202 toward first gas passage 236. For example, check valve 248 may open automatically (e.g., without input or adjustment from a controller or operator) to flow the carrier gas toward vaporizing chamber 202 and close automatically to prevent gas flow toward first gas passage 236. In contrast, shut-off valve 246 may be an electronically or mechanically actuated valve that is operated responsive to input from controller 225 and/or the operator of anesthetic vaporizer 200. For example, shut-off valve 246 may be an on-off valve, where shut-off valve 246 is actuated to an open (e.g., fully open) position that allows gas flow through shut-off valve 246 or a closed (e.g., fully closed) position that prevents (e.g., blocks) gas flow through shut-off valve 246 in response to an appropriate command signal from controller 225. Further, pressure regulator 242 may control a gas pressure within second gas passage 238.

The carrier gas delivered to vaporizing chamber 202 via second gas passage 238 flows through liquid anesthetic agent 210 to form a plurality of gas bubbles 212. The plurality of gas bubbles 212 pass through liquid anesthetic agent 210, becoming saturated with vaporized anesthetic agent, as they rise to the surface of the liquid. As one example, vaporization of the liquid anesthetic agent is affected by an amount of time the gas bubbles 212 spend in the liquid anesthetic agent 210 (which may be controlled for by controlling the level of the liquid anesthetic agent 210 in vaporizing chamber 202, as described above) and a temperature difference between the gas bubbles 212 and the liquid anesthetic agent 210. Therefore, in some examples, a heating element may be coupled to or within vaporizing chamber 202 to increase a temperature of liquid anesthetic agent 210 and provide energy for vaporization (e.g., latent heat of vaporization).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Third gas passage 240 is shown including a shut-off valve 250 and a proportional valve 252 within a manifold heater 254. Shut-off valve 250 may be an electronically or mechanically actuated valve that is adjusted responsive to input from controller 225 and/or the operator. For example, shut-off valve 250 may be an on-off valve, wherein shut-off valve 250 is actuated to an open (e.g., fully open) position that allows gas flow through shut-off valve 250 or a closed (e.g., fully closed) position that prevents (e.g., blocks) gas flow through shut-off valve 250 in response to an appropriate command signal from controller 225. Shut-off valve 250 may be closed to quickly stop the supply of the anesthetic agent to a patient, for example. Proportional valve 252 may be a variable valve, such a continuously variable valve, that may be adjusted by controller 225 between a plurality of positions ranging from a fully open to a fully closed position. For example, as a degree of opening of proportional valve 252 increases, an amount (e.g., flow rate) of vapor flowing from vaporizing chamber 202 to first gas passage 236 (e.g., via third gas passage 240) may increase. Conversely, as the degree of opening of proportional valve 252 decreases, the amount of vapor delivered from vaporizing chamber 202 to first gas passage 236 may decrease. Manifold heater 254 may heat shut-off valve 250 and proportional valve 252 to prevent condensation of the vaporized anesthetic agent at the valves. As a non-limiting example, manifold heater 254 may be operated to maintain shut-off valve 250 and proportional valve 252 at a substantially constant temperature, such as 40° C.

Upstream of the junction with third gas passage 240 and downstream of the junction with second gas passage 238, first gas passage 236 carries the bypass gas portion of the fresh gas flow. The bypass gas does not pass through vaporizing chamber 202. An amount of bypass gas flowing through first gas passage 236 may be adjusted by adjusting the fresh gas flow and may be limited by pressure regulator 242. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via inspiratory port 118 described with respect to FIG. 1). A second mass flow sensor 244 may be coupled to first gas passage 236 downstream of the junction with third gas passage 240 to measure a flow rate of the mixed gas exiting anesthetic vaporizer 200. For example, second mass flow sensor 244 may be an ultrasonic flow meter or a calorimetric mass flow meter. In the case of an ultrasonic flow metering architecture, the output anesthetic agent concentration may be calculated by the difference in the measured time of flight (TOF) between upstream ultrasonic flow sensor 241 and downstream ultrasonic flow sensor 244.

In some embodiments, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. As one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 256 may output a signal to controller 225 indicative of the measured concentration of the anesthetic agent (e.g., the concentration of the anesthetic agent vapor) in the mixed gas. Controller 225 may adjust the position of proportional valve 252 based on the measured concentration received from concentration sensor 256 in order to bring the measured concentration of the anesthetic agent to a desired concentration of the anesthetic agent to deliver to the patient, such as by using a proportional-integral-derivative control architecture.

In addition to receiving signals output by level sensor 224, level sensor 221, concentration sensor 256, first mass flow sensor 241, and second mass flow sensor 244, controller 225 may receive additional signals, including signals from one or more pressure and temperature sensors coupled in various locations throughout anesthetic vaporizer 200. Controller 225 receives the signals from the various sensors of FIG. 2, processes the input data, and employs the various actuators of FIG. 2 to adjust operation of anesthetic vaporizer 200 based on the received signals and instructions stored on a memory of the controller. For example, controller 225 may receive the measured level of liquid anesthetic agent 210 in sump 222 from level sensor 221 and perform a leakage diagnostic, as will be described below with respect to FIG. 4. In response to an indication that a leak is present, the controller may output an alert to the operator via a human-machine interface (HMI) 226 that is operationally connected to the controller (e.g., via wired or wireless communication). Further, data may be input to controller 225 by the operator of anesthetic vaporizer 200 via HMI 226. Thus, HMI 226 may include both a user input device and an output device. The user input device may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator. The output device may include one or more of a display (e.g., anesthesia display device 104 and/or patient monitoring display device 106 of FIG. 1) for providing visual alerts or text-based messages and a speaker for providing audible alerts or messages.

Next, FIG. 3 schematically shows an example timeline 300 illustrating an effect of anesthetic agent leakage at one or more seal locations of an anesthetic vaporizer. The anesthetic vaporizer may be anesthetic vaporizer 200 introduced in FIG. 2. As such, components of FIG. 3 that function the same as components of FIG. 2 are numbered the same and may not be reintroduced. Further, some components of anesthetic vaporizer 200 are not shown or are summarized in timeline 300 of FIG. 3 for simplicity, although it may be understood that such components are present. Controller 225 may execute one or more methods to detect the leakage, such as the methods described below with respect to FIGS. 4-6.

Timeline 300 shows a first snapshot 302 of anesthetic vaporizer 200 at a first time (t1) and a second snapshot 304 of anesthetic vaporizer 200 at a second time (t2). The second time is later than the first time, as shown by a direction of a time axis 301, with an amount of time $\Delta t$ elapsing between the first time and the second time ($\Delta t=t2-t1$). Each snapshot represents an instantaneous depiction of anesthetic vaporizer 200 at the corresponding time, including an amount (e.g., volume) of liquid anesthetic agent 210 in sump 222. For example, first snapshot 302 shows a first level of liquid anesthetic agent 210 at the first time ($level_{t1}$) and a first volume of liquid anesthetic agent 210 at the first time ($V_{t1}$), and second snapshot 302 shows a second level of liquid anesthetic agent 210 at the second time ($level_{t2}$) and a second volume of liquid anesthetic agent 210 at the second time ($V_{t2}$). The first level is greater than the second level, and the first volume is greater than the second volume. As will be described below with respect to FIG. 5, controller 225 may determine the first volume based on the first level, as measured by level sensor 221 at the first time, and the second volume based on the second level, as measured by level sensor 221 at the second time. In the example of timeline 300, the decrease in the volume of anesthetic agent 210 between the first time and the second time is due to anesthetic agent leakage and not due to pump operation. For example, anesthetic vaporizer 200 may be off (e.g., powered down) between the first time and the second time. As another example, anesthetic vaporizer 200 may be on (e.g., powered up), but pump 220 may not be operated to deliver liquid anesthetic agent 210 to vaporizing chamber 202 between the first time and the second time.

Figure 4:
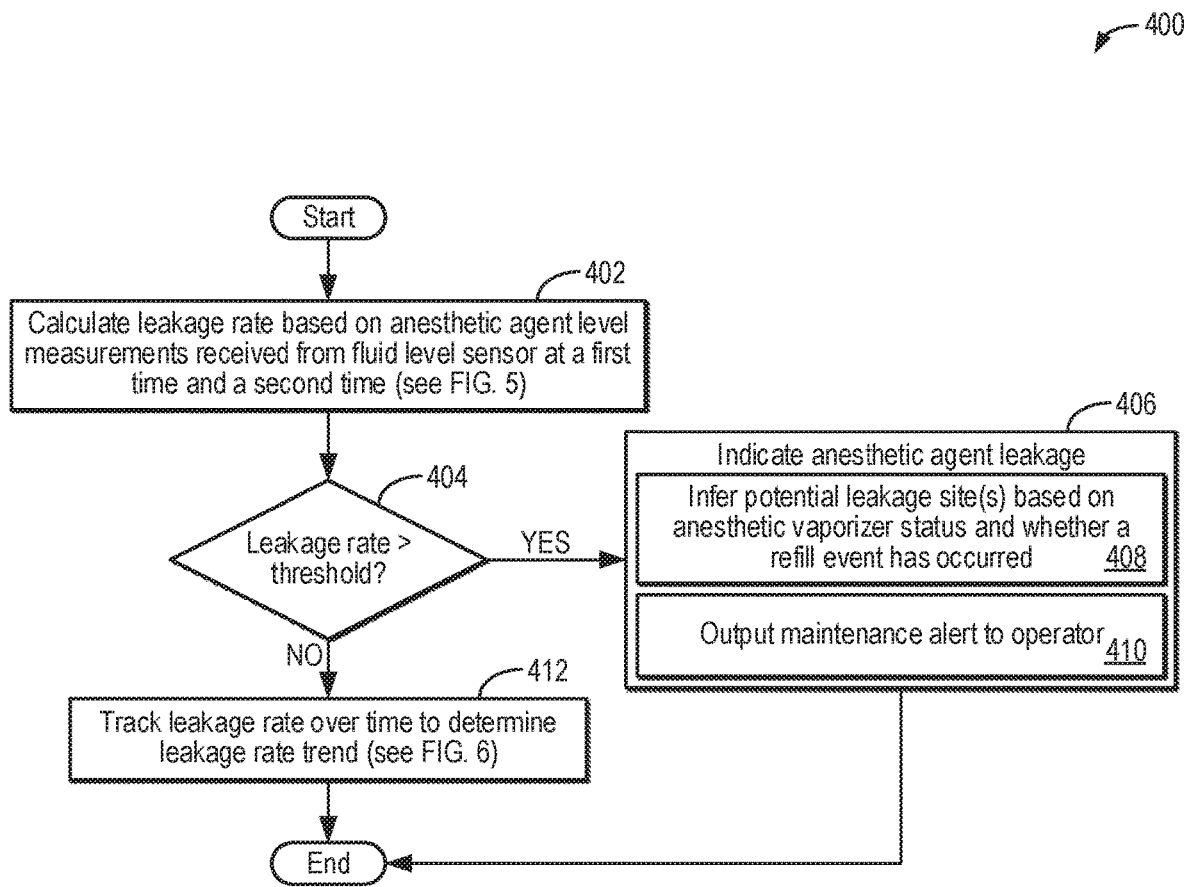
FIG. 4 is a high-level flow chart illustrating an exemplary embodiment of a method for diagnosing anesthetic agent leakage in an anesthetic vaporizer.

The leakage diagnostic described herein with respect to FIG. 4 may be used to identify fill assembly wear and seal leaks, pump leaks, sump component seal leaks, and valve degradation that may lead to anesthetic agent leakage from anesthetic vaporizer 200. Potential leakage sites (e.g., seal locations) through which liquid anesthetic agent 210 or anesthetic agent vapor may escape to atmosphere or other vaporizer locations are highlighted in timeline 300 by dashed circles. However, it may be understood that additional potential leakage sites not illustrated in the example of FIG. 3 may be present, and different anesthetic vaporizer configurations may include leakage sites in different locations. For example, agent leakage may occur at any interface or seal in a wetted path of the anesthetic agent. Thus, the leakage diagnostic described herein is not limited to detecting anesthetic agent leakage at the potential leakage sites shown in FIG. 3 by way of example.

Fill cap 223 represents a first potential leakage site 306. For example, fill cap 223 may include a rubber o-ring seal, which may degrade over time. Anesthetic agent vapor may leak through fill cap 223 when fill cap 223 is not fully secured (e.g., following a refill event) and/or when the seal of fill cap 223 is worn or otherwise degraded, resulting in additional evaporation of liquid anesthetic agent 210 and a corresponding volume decrease within sump 222. An attachment point between fill port 227 and sump 222 provides a second potential leakage site 308. For example, a gas-tight seal between fill port 227 and sump 222 may wear or otherwise degrade over time, enabling anesthetic agent vapor to leak to atmosphere via site 308. Similarly, an attachment point between level sensor 221 and sump 222 provides a third potential leakage site 310 through which anesthetic agent vapor may escape. An attachment point between sump 222 and liquid return line 215 provides a fourth potential leakage site 312 through which anesthetic agent vapor and/or anesthetic agent vapor may leak to atmosphere. Liquid anesthetic agent 210 may leak at a fifth potential leakage site 314 where sump 222 and conduit 214 connect, at a sixth potential leakage site 316 corresponding to pump 220, and at a seventh potential leakage site 318 corresponding to shut-off valve 218. As one example, one or more seals within pump 220 may degrade, causing leakage through pump 220 when pump 220 is not operated to deliver liquid anesthetic agent 210 from sump 222 to vaporizing chamber 202. As another example, shut-off valve 218 may include one or more seals that may become worn or otherwise degrade over time, enabling liquid anesthetic agent 210 to flow through shut-off valve 218 while shut-off valve 218 is commanded closed.

Turning now to FIG. 4, a high-level flow chart of an example method 400 for diagnosing anesthetic agent leakage from an anesthetic vaporizer is shown. Method 400 and the rest of the methods included herein may be executed by a controller, such as controller 225 of FIGS. 2 and 3, according to instructions stored in a memory of the controller (e.g., memory 228 of FIGS. 2 and 3) and in conjunction with one or more sensors (e.g., level sensor 221 of FIGS. 2 and 3) and actuators. As one example, method 400 may be executed to evaluate a static leakage rate based on a change in anesthetic agent volume while the anesthetic vaporizer is shut down. In such an example, a portion of method 400 and (sub-methods included therein) may be performed prior to the shut down, and a remaining portion of method 400 (and sub-methods included therein) may be performed after a subsequent start up, as will be elaborated below. As another example, method 400 may be executed to evaluate an operational leakage rate based on a change in anesthetic agent volume while the anesthetic vaporizer is on and operating. Although method 400 and the rest of the methods included herein will be described with respect to anesthetic vaporizer 200 shown in FIGS. 2 and 3, it may be understood that method 400 may be applied to any anesthetic vaporizer configuration that includes an electronic controller and level sensor.

At 402, a leakage rate is calculated based on anesthetic agent level measurements received from a fluid level sensor (e.g., level sensor 221 shown in FIGS. 2 and 3) at a first time and at a second time. As will be elaborated below with respect to FIG. 5 and as mentioned above, the leakage rate may be a static leakage rate or an operational leakage rate depending on a status of the anesthetic vaporizer between the first time and the second time. For example, the leakage rate may be a static leakage rate when anesthetic vaporizer shutdown is initiated at the first time and anesthetic vaporizer startup is initiated at the second time, resulting in an "off" vaporizer status between the first time and the second time. As another example, the leakage rate may be an operational leakage rate when the pump is currently operating, resulting in an "on" vaporizer status between the first time and the second time.

At 404, it is determined if the leakage rate is greater than a threshold. The threshold may be a pre-calibrated standard allowable leak, which may be anesthetic vaporizer-specific and may further vary on the anesthetic agent being used. As another example, the threshold may vary based on whether the leakage rate is a static leakage rate or an operational leakage rate. As one non-limiting example, the threshold may be in a range of 0.0012 mL/min (e.g., 12 mL/week) to 0.0015 mL/min for both the static leakage rate and the operational leakage rate.

If the leakage rate is greater than the threshold, method 400 proceeds to 406, and anesthetic agent leakage is indicated. Further, one or more potential leakage sites may be inferred based on the anesthetic vaporizer status and whether a refill event has occurred, as indicated at 408. For example, a refill event may be inferred if the anesthetic agent level in the sump has increased since the last leakage diagnostic was performed. If a refill event has occurred, it may be inferred that the leakage is occurring through a fill apparatus, such as due to improper attachment of a fill cap (e.g., fill cap 223 shown in FIGS. 2 and 3). As another example, if the anesthetic vaporizer is on between the first time and the second time (e.g., the leakage rate is an operational leakage rate), it may be inferred that the leakage is occurring at the pump. As still another example, if a rate of agent usage (e.g., a rate of liquid anesthetic agent delivery to a vaporizing chamber of the anesthetic vaporizer) is greater than that predicted from an agent concentration measurement (e.g., as measured by a concentration sensor, such as concentration sensor 256 of FIG. 2), it may be inferred that the leakage is occurring at the pump.

Further still, a maintenance alert may be output to an operator of the anesthetic vapor, as indicated at 410. For example, the controller may communicate the maintenance alert to the operator via a human-machine interface (e.g., HMI 226 shown in FIGS. 2 and 3). As one example, the maintenance alert may include an audible alarm or message. As another example, the maintenance alert may additionally or alternatively include a visual message. The message may include information regarding the leakage (such as that a leakage has been detected, the calculated leakage rate, etc.) as well as the inferred potential leakage sites. The inferred potential leakage sites may guide a service technician during maintenance so that the most probable leakage locations are checked for wear or degradation first, thereby streamlining the maintenance procedure. Further, in some embodiments, the controller may estimate a duration until the liquid anesthetic agent is expected to be depleted based on the calculated leakage rate and a currently measured anesthetic agent level, and the estimated duration may be included in the maintenance alert. Additionally, in some embodiments, when the leakage rate is a static leakage rate, the controller may prevent the anesthetic vaporizer from being operated, such as by disabling the anesthetic vaporizer. However, if the leakage rate is an operational leakage rate and the anesthetic vaporizer is already in use, the controller may not disable the anesthetic vaporizer until after anesthetic agent delivery ends. Method 400 may then end.

Returning to 404, if the leakage rate is not greater than the threshold, method 400 proceeds to 412, and the leakage rate is tracked over time to determine a leakage rate trend. As will be described below with respect to FIG. 6, the leakage rate trend may be used to determine if the leakage rate is increasing over time, such as due to increasing degradation of a seal. If the leakage rate is increasing over time, the controller may estimate an amount of time remaining until the leakage rate increases above the threshold so that the controller may pre-emptively alert the operator to have the anesthetic vaporizer serviced within the estimated amount of time. Method 400 may then end.

Figure 5:
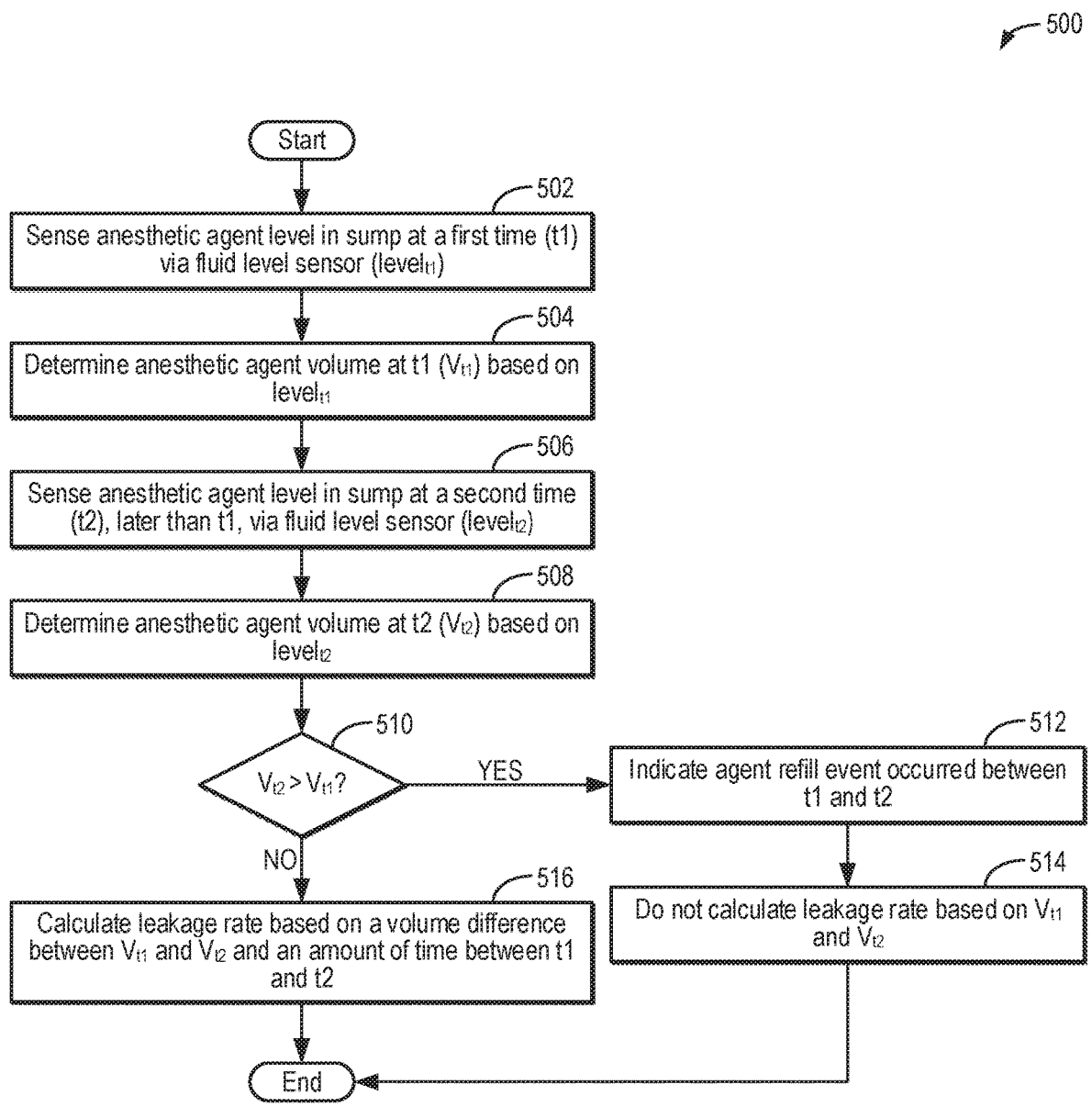
FIG. 5 is a flow chart illustrating an exemplary embodiment of a method for calculating an anesthetic agent leakage rate based on measurements made by a fluid level sensor.

Continuing to FIG. 5, an example method 500 is provided for calculating a leakage rate of an anesthetic agent from an anesthetic vaporizer based on measurements received from a fluid level sensor (e.g., level sensor 221 shown in FIGS. 2 and 3). For example, method 500 of FIG. 5 may be performed by a controller (e.g., controller 225 of FIGS. 2 and 3) as a part of method 400 of FIG. 4 (e.g., at 402). In one embodiment, method 500 may be executed responsive to anesthetic vaporizer shutdown being initiated in order to calculate a static leakage rate. In another embodiment, method 500 may be executed responsive to completion of a pump pulse while the anesthetic vaporizer is on and operating in order to calculate an operational leakage rate. Therefore, two embodiments of method 500 will be described below.

At 502, an anesthetic agent level in a sump of the anesthetic vaporizer is sensed at a first time (t1) via the fluid level sensor. The sensed (e.g., measured) anesthetic agent level at the first time corresponds to $level_{t1}$ of FIG. 3, for example. The controller may store the sensed anesthetic agent level at the first time to memory (e.g., memory 228 shown in FIGS. 2 and 3) along with a timestamp corresponding to the first time, which may include both date and time information. In a first embodiment of method 500, shutdown of the anesthetic vaporizer is initiated at the first time. For example, the controller may receive a shutdown request and, responsive to the shutdown request, obtain $level_{t1}$ from the fluid level sensor and store $level_{t1}$ to memory prior to powering down the anesthetic vaporizer. In a second embodiment of method 500, the anesthetic vaporizer is on and operating, and a pump pulse is completed just before the first time. For example, the controller may send a control signal to the pump to operate the pump at less than 100% duty cycle. The control signal may include an "on" duration, during which the pump actively delivers anesthetic agent from a sump to a vaporizing chamber (e.g., the pump pulse), and an "off" duration, during which the pump does not deliver anesthetic agent to the vaporizing chamber. Thus, the first time may correspond to a beginning of the "off" duration of the control signal, following completion of the "on" duration.

At 504, an anesthetic agent volume at the first time ($V_{t1}$) is determined based on $level_{t1}$. The anesthetic agent volume at the first time corresponds to $V_{t1}$ of FIG. 3, for example. Determining $V_{t1}$ based on $level_{t1}$ may include inputting $level_{t1}$ into a function or look-up table stored in memory, for example, which may output the corresponding volume for the input level. The function or look-up table may relate fluid level measurements made by the fluid level sensor to volume amounts based on a known geometry of the sump. The controller may save $V_{t1}$ to memory along with a timestamp corresponding to the first time. In some examples, the controller may delete $level_{t1}$ from memory after saving $V_{t1}$ to memory. In other examples, the controller may continue storing $level_{t1}$ in memory after saving $V_{t1}$ to memory. Further, the first embodiment of method 500 may include determining $V_{t1}$ prior to shutting down the anesthetic vaporizer or after the anesthetic vaporizer is restarted.

At 506, an anesthetic agent level in the sump is sensed at a second time (t2), which is later than the first time, via the fluid level sensor. The sensed anesthetic agent level at the second time corresponds to $level_{t2}$ of FIG. 3, for example. The controller may store the sensed anesthetic agent level at the second time to memory along with a timestamp corresponding to the second time. In the first embodiment of method 500, startup of the anesthetic vaporizer is initiated at the second time. For example, the controller may obtain $level_{t2}$ from the fluid level sensor responsive to the startup of the anesthetic vaporizer being initiated. The startup is a next startup of the anesthetic vaporizer following the shutdown initiated at the first time (e.g., at 502), sequential in order with no intervening startups and shutdowns in between. In the second embodiment of method 500, the second time occurs just before commencing a subsequent pump pulse. For example, the second time may correspond to an end of the "off" duration of the control signal, prior to the next "on" duration. The subsequent pump pulse is sequential in order with the pump pulse completed at the first time (e.g., at 502), with no intervening pump pulses in between.

At 508, an anesthetic agent volume at the second time ($V_{t2}$) is determined based on $level_{t2}$. For example, the controller may input $level_{t2}$ into a function or look-up table stored in memory, which may output the corresponding volume for the input level, as described above at 504. The controller may save $V_{t2}$ to memory along with a timestamp corresponding to the second time. In some examples, the controller may delete $level_{t2}$ from memory after saving $V_{t2}$ to memory. In other examples, the controller may continue storing $level_{t2}$ in memory after saving $V_{t2}$ to memory.

At 510, it is determined if $V_{t2}$ is greater than $V_{t1}$. For example, the controller may directly compare $V_{t2}$ with $V_{t1}$ in order to determine whether or not to calculate the leakage rate. For example, the leakage rate may be calculated when $V_{t2}$ is less than $V_{t1}$, indicating that the volume of anesthetic agent in the sump has decreased between the first time and the second time, but not when $V_{t1}$ is less than $V_{t2}$, indicating that the volume of anesthetic agent in the sump has increased between the first time and the second time.

If $V_{t2}$ is greater than $V_{t1}$, method 500 proceeds to 512, and it is indicated that an agent refill event has occurred between t1 and t2. For example, the controller may log the agent refill event to memory, which may be used for leakage diagnostics (e.g., for inferring potential leakage sites, as described above at 408 of method 400), for anesthetic agent usage tracking, etc.

At 514, a leakage rate is not calculated based on $V_{t1}$ and $V_{t2}$. For example, even if leakage had occurred between t1 and t2, the increase in volume between t1 and t2 prevents leakage detection, and method 500 ends. However, method 500 may be repeated responsive to an initiation of a subsequent shutdown or a completion of a subsequent pump pulse, enabling the leakage diagnostic to be reattempted.

Returning to 510, if $V_{t2}$ is not greater than $V_{t1}$ (e.g., $V_{t2}$ is less than or equal to $V_{t1}$), method 500 proceeds to 516, and the leakage rate is calculated based on a volume difference between $V_{t1}$ and $V_{t2}$ and an amount of time (e.g., elapsed duration) between t1 and t2. For example, the amount of time between t1 and t2 may correspond to Δt of FIG. 3. The controller may calculate the leakage rate (L) based on $V_{t1}$, $V_{t2}$, t1, and t2 using a predetermined equation stored in memory, such as the equation:

$$L = \frac{V_{t1} - V_{t2}}{t2 - t1}.$$

Further, the calculated leakage rate may be saved to memory along with a timestamp for future logistics. As described above with respect to FIG. 4, the controller may compare the leakage rate to a threshold to determine if anesthetic agent leakage is occurring. Further, as described below with respect to FIG. 6, the controller may track the leakage rate over time to determine a leakage rate trend. Method 500 then ends.

Figure 6:
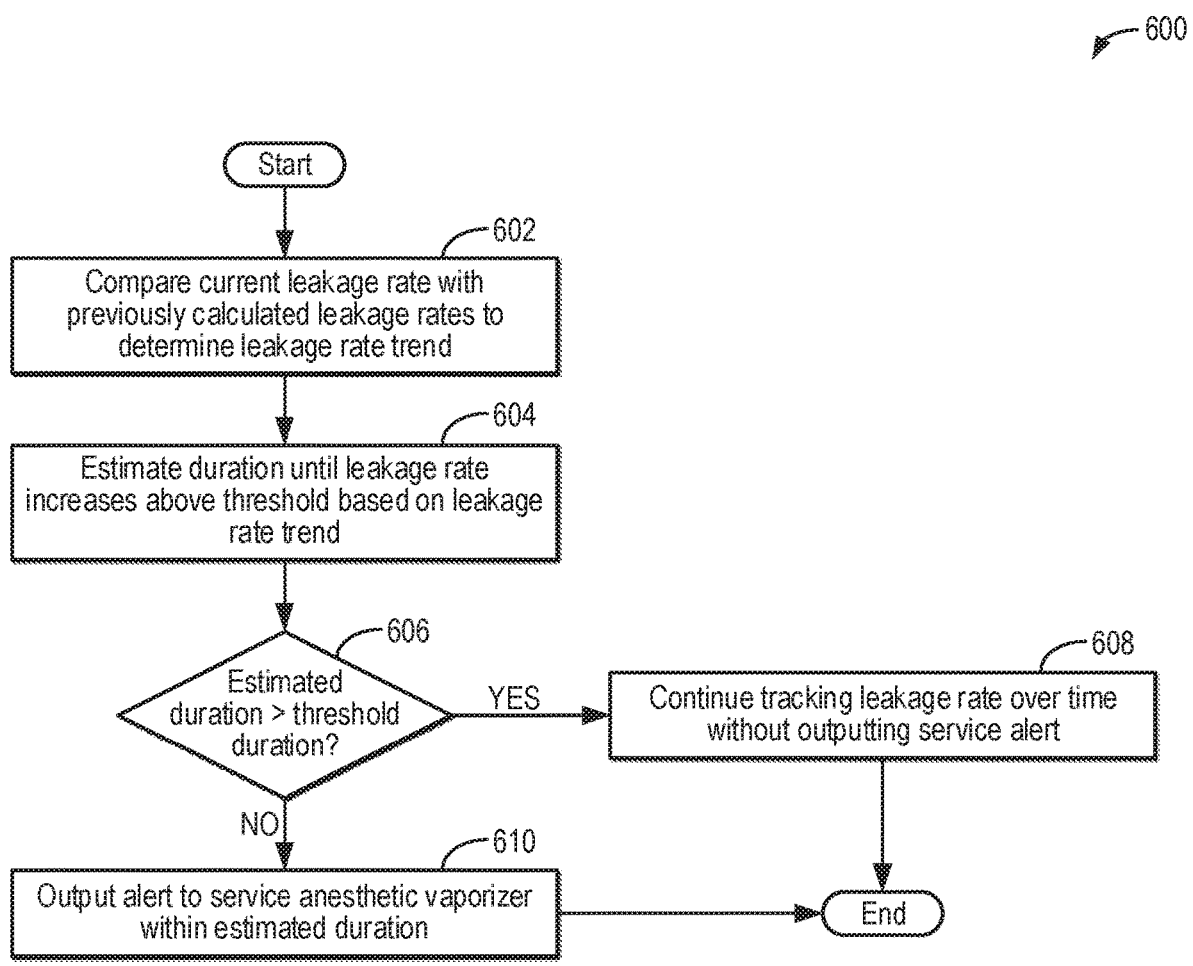
FIG. 6 is a flow chart illustrating an exemplary embodiment of a method for tracking an anesthetic agent leakage rate over time to anticipate anesthetic vaporizer maintenance.

Next, FIG. 6 shows an example method 600 for tracking a leakage rate of an anesthetic vaporizer over time. Method 600 of FIG. 6 may be performed by a controller (e.g., controller 225 of FIGS. 2 and 3) as a part of method 400 of FIG. 4 (e.g., at 412). For example, method 600 may be executed responsive to the leakage rate remaining below a threshold for indicating an immediate maintenance alert (described above at 404 of FIG. 4).

At 602, a current leakage rate is compared with previously calculated leakage rates to determine a leakage rate trend. The current leakage rate corresponds to a most recently calculated leakage rate. As mentioned above at 510 of FIG. 5, once calculated, leakage rates may be stored to memory along with date and time information. Thus, the controller may access the previously calculated leakage rates from memory. In some embodiments, the previously calculated leakage rates may be reset following a service event, such as in response to input from a service technician indicating that maintenance has been performed (e.g., seal replacement). In other embodiments, an additional data point may indicate the service event, and the controller may only use leakage rates calculated after the service event data point in the comparison. In still other embodiments, the controller may continue storing all captured data points but may create a new and separate datalog table following the service event data point so that leakage rates calculated after the service event are stored separately from the leakage rates calculated before the service event. For example, the current leakage rate may be compared with the previously calculated leakage rates stored in the most recently created datalog table only. Further, the previously calculated leakage rates may correspond to a same type of leakage rate as the current leakage rate (e.g., static or operational, which may be stored separately, such as in separate datalog tables). In this way, the controller may use relevant leakage rate data for determining the leakage rate trend while excluding data that may confound the trend.

The controller may determine the leakage rate trend using an algorithm, where the current leakage rate and the previously calculated leakage rates are inputs of the algorithm and the leakage rate trend is the output of the algorithm. In one embodiment, the algorithm a statistical process control algorithm. As an example, the statistical process control algorithm may utilize a chart style of data evaluation, in which the data is evaluated for shifts and outliers. The leakage rate at each time point may be plotted over time, where the leakage rate is the vertical axis and time is the horizontal axis. The controller may evaluate the chart for trends, such as shifts in the data over time (e.g., a slope of the data). Further, the statistical process control algorithm may evaluate the data for random (e.g., stochastic) variation and confirm that each included data point fits within desired evaluation limits (e.g., between 0.0001 mL/min and 0.0012 mL/min, which may be the threshold for indicating an immediate maintenance alert in method 400 of FIG. 4).

In another embodiment, the algorithm is a predictive or forecasting algorithm that uses the current and previously calculated leakage rates as a time-based data set. For example, the algorithm may use a basic time function, such as $f(t)=mx+b$, where m is the slope of the time-based data set, x is the time, and b is the calculated leakage rate at time t0 (e.g., the first calculated leakage rate in the data set). As an example, the leakage rate trend may be equal to m. As another example, additionally or alternatively, the predictive or forecasting algorithm may include a time-based exponential smoothing algorithm. The time-based data sequence that is input to the exponential smoothing algorithm may be represented as $x\{t\}$ (e.g., the calculated leakage rate at a given time), and the output of the exponential smoothing algorithm may be represented as $s\{t\}$. The exponential smoothing algorithm may use the formulas $s_0=x_0$, corresponding to the smoothing algorithm output at time t0, and $s_t=\alpha x_t+(1-\alpha)s_{t-1}$, where time is greater than t0 and a is a smoothing factor ($0<\alpha<1$). The output of the exponential smoothing algorithm may give an estimate of what the next value of x will be. As an example, when x is estimated as a greater value than the currently calculated leakage rate, the leakage rate may be increasing.

At 604, a duration until the leakage rate increases above the threshold is estimated based on the leakage rate trend. For example, the controller may input the leakage rate trend into a look-up table, algorithm, or function stored in memory, which may output the estimated duration. The algorithm may be a predictive or forecasting algorithm, for example. As another example, the algorithm may be included in (e.g., a part of) the algorithm used at 602 above to determine the leakage rate trend. As an example, as the leakage rate trend increases (e.g., becomes more positive, indicating that the leakage rate is at least generally increasing over time), the estimated duration until the leakage rate is expected to increase above the threshold decreases. Conversely, as the leakage rate trend decreases (e.g., becomes less positive), the estimated duration until the leakage rate is expected to increase above the threshold increases.

At 606, it is determined if the estimated duration is greater than a threshold duration. The threshold duration may be a non-zero, pre-calibrated time duration above which indicating future maintenance may be premature. As one example, when the estimated duration is greater than the threshold duration, the leakage rate trend may be relatively small, such as when the leakage rate is relatively stable and/or the leakage rate is relatively small (e.g., less than or equal to 0.001 mL/min). In such an example, the accuracy of the estimated duration may be decreased. Further, the threshold duration may be calibrated to provide sufficient time to schedule a service event before the leakage rate is expected to increase above the threshold leakage rate.

If the estimated duration is greater than the threshold duration, method 600 proceeds to 608, and the leakage rate continues to be tracked over time without a service alert being output. For example, each newly calculated leakage rate may be stored to memory and compared with the previously calculated leakage rates responsive to the newly calculated leakage rate remaining below the threshold leakage rate. Method 600 may then end.

If instead the estimated duration is not greater than the threshold duration at 606 (e.g., the estimated duration is less than or equal to the threshold duration), method 600 proceeds to 610, and an alert to service the anesthetic vaporizer within the estimated duration is output. For example, the controller may output the alert via a human-machine interface (e.g., HMI 226 shown in FIGS. 2 and 3). As one example, the alert may include an audible alarm or message. As another example, the alert may additionally or alternatively include a visual message. The message may indicate that anesthetic vaporizer service is recommended within the estimated duration to prevent degraded vaporizer performance and downtime, for example. In some examples, the message may further indicate that the leakage rate is increasing but currently remains below the threshold for immediate maintenance. The message may be communicated to an operator of the anesthetic vaporizer, for example. Following 610, method 600 may end.

Thus, the systems and methods described herein provide for electronically detecting and tracking leakage of an anesthetic agent from an anesthetic vaporizer. As a result, leakage may be promptly and accurately detected without external leak detection equipment and manual leak tests. Further, once detected, the systems and methods described herein include outputting a maintenance alert to either service the anesthetic vaporizer immediately or within a specified time frame, estimated based on changes in the leakage over time. Further still, the systems and methods described herein provide maintenance information to help target where the leakage is occurring. As a result, anesthetic vaporizer maintenance may be expedited, and maintenance costs may be decreased by only replacing degraded components that are causing the leakage.

A technical effect of automatically diagnosing anesthetic agent leakage from an anesthetic vaporizer based on measurements from an electronic level sensor is that anesthetic agent leakage may be detected as it occurs and without additional leak detection equipment, thereby increasing anesthetic vaporizer performance and decreasing maintenance time.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for diagnosing anesthetic agent leakage from an anesthetic vaporizer, comprising:
 calculating a leakage rate based on measurements of an anesthetic agent level in a sump of the anesthetic vaporizer, the measurements received from a fluid level sensor at a first time and a second time;
 responsive to the leakage rate exceeding a first threshold during a first operational status or a second threshold during a second operational status, inferring potential leakage sites of the anesthetic vaporizer based on the anesthetic vaporizer being in the first operational status or the second operational status, wherein the anesthetic vaporizer being in the first operational status indicates potential leakage sites at a first location and the anesthetic vaporizer being in the second operational status indicates potential leakage sites at a second location, wherein the second location is different than the first location; and
 outputting a maintenance alert including the inferred potential leakage sites responsive to the leakage rate exceeding the first threshold or the second threshold.

2. The method of claim 1, further comprising:
 comparing the leakage rate to a plurality of previously calculated leakage rates to determine a leakage rate trend responsive to the leakage rate remaining below the first threshold or the second threshold;
 estimating a duration until the leakage rate increases above the first threshold or the second threshold based on the leakage rate trend;
 in response to the estimated duration being less than or equal to a threshold duration, outputting a maintenance alert including the estimated duration; and
 in response to the estimated duration being greater than the threshold duration, tracking the leakage rate over time without outputting the maintenance alert including the estimated duration.

3. The method of claim 1, wherein calculating the leakage rate based on the measurements comprises:
 sensing a first anesthetic agent level during the first operational status via the fluid level sensor;
 determining a first volume of anesthetic agent based on the first anesthetic agent level;
 sensing a second anesthetic agent level during the second operational status via the fluid level sensor;
 determining a second volume of anesthetic agent based on the second anesthetic agent level; and
 calculating the leakage rate as a ratio of a change in volume between the first volume of anesthetic agent and the second volume of anesthetic agent.

4. The method of claim 1, wherein the first operational status is at a shutdown of the anesthetic vaporizer and the second operational status is at a next startup of the anesthetic vaporizer following the shutdown.

5. The method of claim 4, wherein the leakage rate is a measure of anesthetic agent leakage while the anesthetic vaporizer is in the second operational status.

6. The method of claim 1, wherein the first operational status is at a completion of a pulse of a pump coupled to the sump and the second operational status is prior to a commencement of a next pulse of the pump.

7. The method of claim 6, wherein the leakage rate is a measure of anesthetic agent leakage while the anesthetic vaporizer is in the first operational status.

8. The method of claim 1, wherein a refill event occurring within a threshold duration before the first operational status indicates potential leakage sites at a third location.

9. The method of claim 8, wherein the refill event includes an increase in the anesthetic agent level measured by the fluid level sensor.

10. A system for an anesthetic vaporizer, comprising:
 a sump;
 a fluid level sensor positioned to measure a level of liquid anesthetic agent in the sump; and
 a controller storing executable instructions in non-transitory memory that, when executed, cause the controller to:
  calculate a leakage rate based on measurements of the level of the liquid anesthetic agent in the sump received from the fluid level sensor during a first operational state and a second operational state;
  output a maintenance alert responsive to the leakage rate exceeding a first threshold in the first operational state or a second threshold in the second operational state, and output inferred potential leakage sites responsive to the anesthetic vaporizer being in the first operational state or the second operational state, wherein the anesthetic vaporizer being in the first operational state when the leakage rate exceeds the first threshold indicates a leak at a first position and the anesthetic vaporizer being in the second operational state when the leakage rate exceeds the second threshold indicates a leak at a second position, wherein the first and second positions are different.

11. The system of claim 10, wherein the controller stores further instructions in non-transitory memory that, when executed, cause the controller to:
  determine a leakage rate trend by comparing the leakage rate to a plurality of previously calculated leakage rates responsive to the leakage rate remaining below the first threshold or the second threshold;
  estimate a duration until the leakage rate increases above the first threshold or the second threshold based on the leakage rate trend;
  output a maintenance alert including the estimated duration in response to the estimated duration being less than or equal to a threshold duration; and
  track the leakage rate over time without outputting the maintenance alert including the estimated duration in response to the estimated duration being greater than the threshold duration.

12. The system of claim 10, wherein the instructions that cause the controller to calculate the leakage rate based on the measurements include further instructions stored in non-transitory memory that, when executed, cause the controller to:
  sense a first anesthetic agent level during the first operational state via the fluid level sensor;
  determine a first volume of the liquid anesthetic agent based on the first anesthetic agent level;
  sense a second anesthetic agent level during the second operational state via the fluid level sensor;
  determine a second volume of the liquid anesthetic agent based on the second anesthetic agent level; and
  calculate the leakage rate based on a change in volume between the first volume and the second volume and an amount of time between the anesthetic vaporizer being in the first operational state and the second operational state.

13. The system of claim 10, wherein the first operational state is at a shutdown of the anesthetic vaporizer and the second operational state is at a next startup of the anesthetic vaporizer following the shutdown.

14. The system of claim 10, further comprising a vaporizing chamber and a pump positioned to deliver the liquid anesthetic agent from the sump to the vaporizing chamber, and wherein the first operational state is at a completion of a pulse of the pump and the second operational state is prior to a commencement of a next pulse of the pump.

15. A non-transitory computer-readable medium comprising instructions that, when executed, cause a processor to:
  calculate a leakage rate of an anesthetic agent from a sump of an anesthetic vaporizer based on level measurements of the anesthetic agent in the sump, the level measurements received from a fluid level sensor during a first operational state and a second operational state;
  infer potential leakage sites of the anesthetic vaporizer responsive to the leakage rate exceeding a first threshold during the first operational state or a second threshold during the second operational state and whether a refill event occurred within a threshold duration before the first operational state; and
  output a maintenance alert including the inferred potential leakage sites responsive to the leakage rate exceeding the first threshold during the first operational state or the second threshold during the second operational state, wherein inferring the potential leakage sites includes selecting a subset of seal locations from a plurality of predefined seal locations.

16. The computer-readable medium of claim 15, comprising further instructions that, when executed, cause the processor to:
  determine a leakage rate trend responsive to the leakage rate remaining below the first threshold or the second threshold by comparing the leakage rate to a plurality of previously calculated leakage rates;
  estimate a duration until the leakage rate increases above the first threshold or the second threshold based on the leakage rate trend;
  output a maintenance alert including the estimated duration in response to the estimated duration being less than or equal to a threshold duration; and
  track the leakage rate over time without outputting the maintenance alert including the estimated duration in response to the duration being greater than the threshold duration.

17. The computer-readable medium of claim 15, wherein, to calculate the leakage rate of the anesthetic agent from the sump of the anesthetic vaporizer based on the level measurements, the instructions, when executed, cause the processor to:
  operate the fluid level sensor to measure a first level of the anesthetic agent in the sump during the first operational state;
  determine a first volume of the anesthetic agent in the sump during the first operational state based on the first level;
  operate the fluid level sensor to measure a second level of the anesthetic agent in the sump during the second operational state;
  determine a second volume of the anesthetic agent in the sump at the second time during the second operational state based on the second level; and
  calculate the leakage rate as a difference between the first volume and the second volume divided by an amount of time between a start of the first operational state and a start of the second operational state.

18. The computer-readable medium of claim 17, wherein, to estimate the duration until the leakage rate increases above the first threshold or the second threshold based on the leakage rate trend, the instructions, when executed, cause the processor to decrease the duration as the leakage rate trend increases and increase the duration as the leakage rate trend decreases.

* * * * *